US006786253B2

(12) United States Patent
Feygin (10) Patent No.: US 6,786,253 B2
(45) Date of Patent: Sep. 7, 2004

(54) ARTICLE COMPRISING A MULTI-CHANNEL DISPENSING HEAD

(75) Inventor: Ilya Feygin, Mountainside, NJ (US)

(73) Assignee: Pharmacopeia, Inc., Princeton, NJ (US)

( * ) Notice: Subject to any disclaimer, the term of this patent is extended or adjusted under 35 U.S.C. 154(b) by 6 days.

(21) Appl. No.: 10/660,251

(22) Filed: Sep. 11, 2003

(65) Prior Publication Data

US 2004/0045626 A1 Mar. 11, 2004

Related U.S. Application Data

(62) Division of application No. 10/088,150, filed on Mar. 13, 2002, now Pat. No. 6,644,364, which is a continuation of application No. PCT/US00/25162, filed on Sep. 14, 2000.
(60) Provisional application No. 60/153,879, filed on Sep. 14, 1999.

(51) Int. Cl.[7] ................................................. B65B 1/04

(52) U.S. Cl. ........................ 141/130; 141/237; 248/75

(58) Field of Search ............................... 141/129, 130, 141/234–246; 422/99, 100; 73/864.17, 864; 222/173, 185.1, 180, 181.1; 137/343; 108/50.11, 50.1; 248/75

(56) References Cited

U.S. PATENT DOCUMENTS 5,988,236 A * 11/1999 Fawcett ....................... 141/130

* cited by examiner

Primary Examiner—Steven O. Douglas
(74) Attorney, Agent, or Firm—DeMont & Breyer (57) ABSTRACT

A multi-channel fluid dispenser includes a reservoir with multiple internal chambers, a multi-channel liquid dispensing head, a plurality of fluid-delivery conduits, and support and positioning elements. The fluid-delivery conduits receive liquid from the chambers in the reservoir and deliver it to the dispensing head. The support and positioning elements are operable to support and position the dispensing head so that it can deliver the liquid from the reservoir to an underlying receiver. The fluid-delivery conduits include one or more optional flow control features that improve the accuracy of the dispensing operation. The multi-channel liquid dispensing head, which includes a valve-support member, a plurality of valves and a plurality of nozzles, is advantageously movable in three directions to facilitate alignment with an underlying receiver. Movement of the dispensing head along two axes is provided by the simple expedient of elongate holes having their long axes aligned in mutually orthogonal directions. In some embodiments, the valves are tiltable away from the vertical so that liquid dispensed from such tilted valves is directed at a non-normal angle into a receiver.

18 Claims, 4 Drawing Sheets

ARTICLE COMPRISING A MULTI-CHANNEL DISPENSING HEAD

STATEMENT OF RELATED APPLICATIONS

This application claims priority of Provisional Application 60/153,879 filed Sep. 14, 1999. This application is a division of U.S. Pat. app. Ser. No. 10/088,150, filed Mar. 13, 2002, now U.S. Pat. No. 6,644,364, which is a 371 of PCT/US00/25162, filed Sep. 14, 2000.

FIELD OF THE INVENTION

The present invention relates to liquid dispensers. More particularly, the present invention relates to a multi-channel liquid dispenser capable of dispensing very small volumes of fluid.

BACKGROUND OF THE INVENTION

Pharmaceutical, combinatorial chemistry, high-throughput screening, and medical diagnostics applications, among others, require dispensing very small volumes of liquid (ie., nano-liters to micro-liters) into a receiver such as a micro-titer plate. It is usually necessary to perform the dispensing operation without cross-contamination, which might occur, for example, if a reagent is being added to a receiver that already contains another reagent.

To substantially eliminate the incidence of cross-contamination, a "non-touch off" method of liquid dispensing is typically used. In this method, a droplet being dispensed does not contact the receiver (or liquid or other material in the receiver) until the droplet completely disengages from the tip of the dispenser. Non-touch-off dispensing requires supplying enough kinetic energy-to a liquid droplet for it to overcome the surface tension of the dispensing tip and enough kinetic energy so that it can be accurately and reliably directed to a desired destination.

Non-touch off dispensing of liquid volumes between about 0.1 to about 5 micro-liters is performed using either shake-off methods or implemented with various valve mechanisms that apportion the dispensed volume. While the use of valves for this service is straightforward in principle, it is rather difficult to implement in practice.

One valve-based prior art technique dispensing technique is the "positive displacement" method. In this method, liquid is pressurized into a valve, typically using a syringe or pump, while a synchronized valve controller opens and closes the valve to expel the liquid. This technique has several drawbacks.

First, the accuracy of the dispensing operation is highly dependent upon the precise coordination of all controls, and is a strong function of the elasticity of the liquid channel and temperature. Moreover, accuracy is affected by the presence of trapped or internally released gas bubbles.

Second, this technique suffers from an unavoidable drop in liquid pressure during each dispensing cycle. As a consequence of the pressure drop, only a portion of the liquid that is advanced to the valve for dispensing each cycle is actually dispensed. This drop in pressure is caused by the delay between pump/syringe action and high-speed valve operation. While certain feedback and sensory elements can improve or at least monitor the operation, the design and implementation of the system becomes quite complicated.

There are some additional drawbacks that affect most prior art liquid dispensers regardless of operating principles. For instance, in most prior art liquid dispensers, liquid travels a relatively large distance through tubing, etc., to reach the dispensing valve. This long travel distance might result in changes in liquid volume due to temperature/viscosity fluctuations, internal gas bubbles, elasticity variations of the tubing, and the like. Moreover, long tubing runs generally result in reagent losses during priming, cleaning and servicing operations.

Furthermore, most prior art liquid dispensers (especially multi-head liquid dispensers) are expensive. The expense is related to, among other elements, relatively complex positioning devices that position the dispensing heads.

There is a need, therefore, for a liquid dispenser that is capable of high-speed liquid delivery and is simpler, more reliable and less expensive than existing dispensers.

SUMMARY OF THE INVENTION

In accordance with some embodiments of the present invention, a multichannel fluid dispenser that avoids some of the problems of the prior art is disclosed.

In the illustrative embodiment, a multi-channel fluid dispenser includes a reservoir, a multi-channel liquid dispensing head, a plurality of fluid-delivery conduits, and support and positioning elements.

The reservoir advantageously has multiple internal chambers for segregating liquid within the reservoir, as well as a non-compartmentalized region that overlies the chamnbers. The non-compartmentalized region facilitates an even distribution of pressure within the reservoir, thereby promoting the balanced dispensing of liquids from the various chambers.

The fluid-delivery conduits receive liquid from the chambers in the reservoir and deliver it to the dispensing head. The support and positioning elements are operable to support and position the dispensing bead so that it can deliver the liquid from the reservoir to an underlying receiver.

In some embodiments of the invention, the multi-channel liquid dispensing head includes a valve-support member, a plurality of valves and a plurality of nozzles. The multi-channel liquid dispensing head is supported by a positioning member that engages the valve support plate.

The multi-channel liquid dispensing head is advantageously movable along three-axis to facilitate alignment with an underlying receiver. In one embodiment of the invention, elongate holes in the positioning member and elongate holes in the valve-support member cooperate to provide two-axis positioning. A separate positioning mechanism provides movement along the third axis.

In one embodiment of the present invention, the valves are attached the valve-support member by a fastener, such as a nut. The valves are received by an eccentrically-disposed hole in the fastener. Due to the eccentrically-disposed hole, as the fastener is rotated, the valves tilt relative to the vertical and the liquid dispensed from such tilted valves is directed at a non-normal angle into a receiver.

In further embodiments, the fluid-delivery conduits include one or more optional flow control features that improve the accuracy of the dispensing operation. These and other features of the present invention are described in further detail in the Detailed Description with reference to the attached drawing Figures.

DETAILED DESCRIPTION

Figure 1:
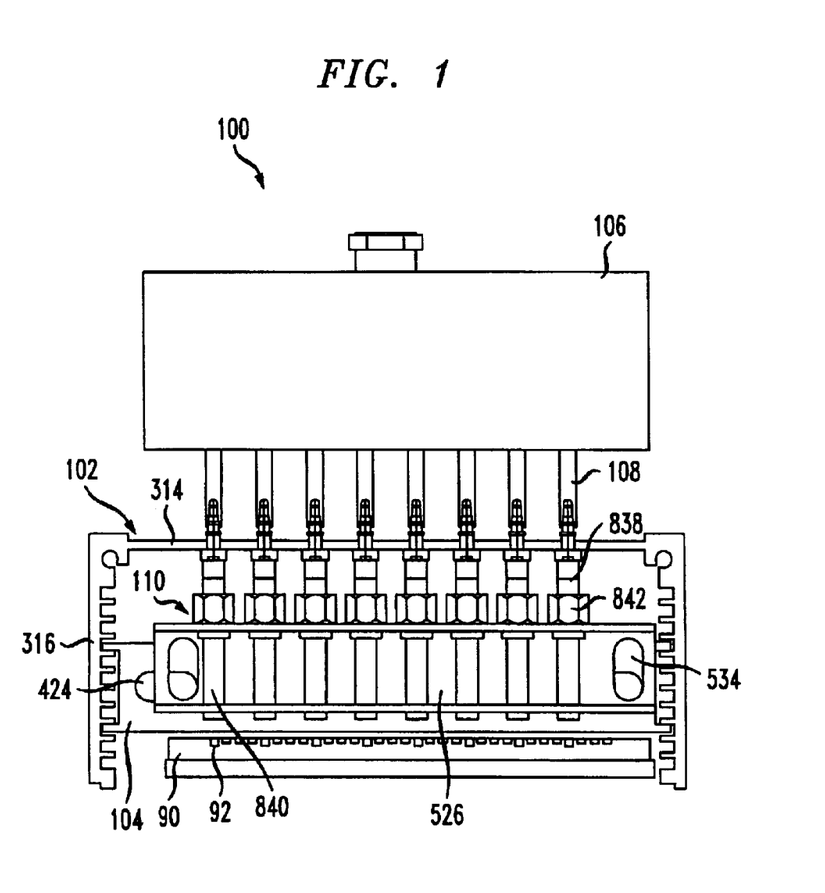
FIG. 1 depicts a front-view of a multi-channel dispenser in accordance with the illustrative embodiment of the present invention.
Figure 2:
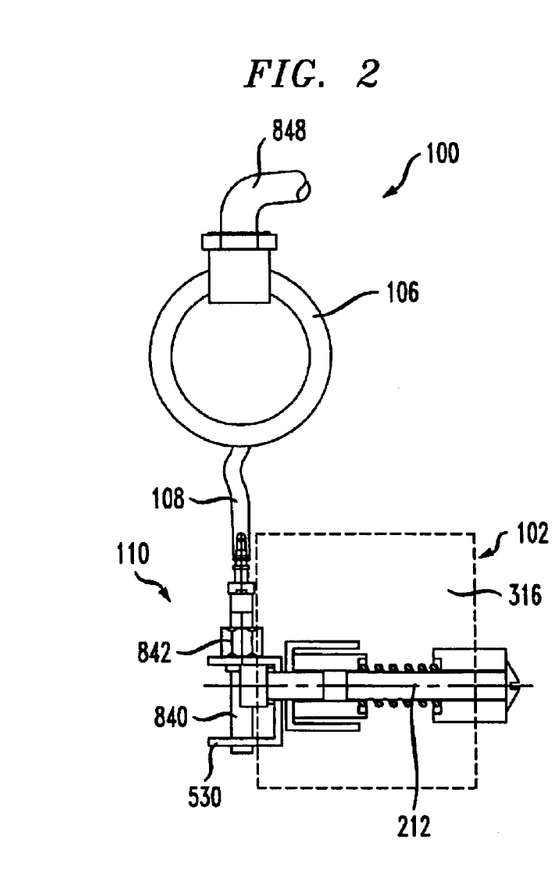
FIG. 2 depicts a cross-sectional side view of the dispenser shown in FIG. 1.

FIG. 1 (front view) and FIG. 2 (side view) depict multi-channel dispenser 100 in accordance with the illustrative embodiment of the present invention. Dispenser 100 comprises support member 102, horizontally-disposed positioning member 104, reservoir 106, a plurality of fluid-delivery conduits 108 and multi-channel liquid dispensing head 110, interrelated as shown. Multi-channel liquid dispensing head 110 comprises valve-support member 526, and a plurality of valves 838 with integrated nozzles 840.

Liquid that is stored in reservoir 106 is delivered, under pressure, to valves 838, via fluid-delivery conduits 108. The liquid that is delivered to valves 838 is dispensed to an underlying receiver, such as micro-titer plate 90.

Illustrative multi-channel dispenser 100 depicted in FIGS. 1 and 2 is functionally segregated into two portions: a support and positioning portion, and a dispensing portion. The support and positioning portion comprises, in some embodiments of the present invention, support member 102, horizontally-disposed positioning member 104, valve-support member 526 and longitudinal positioner 212 (see FIG. 2). The dispensing portion comprises reservoir 106, fluid-delivery conduits 108, dispensing valves 838 and integrated nozzles 840.

The Support and Positioning Portion

The support and positioning portion of multi-channel dispenser 100 supports the dispensing portion and advantageously facilitates placing the dispensing portion in a position that is suitable for dispensing fluid into a receiver.

The basic configuration for the support and positioning portion has support member 102 receiving positioning member 104 that in turn receives valve-support plate 526.

Figure 3:
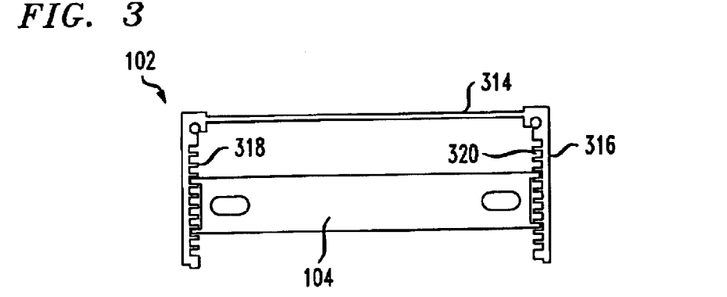
FIG. 3 depicts a u-shaped support member that supports a multi-channel liquid dispensing head.

With reference to FIGS. 1 and 3, illustrative support member 102 is "u-shaped," having top 314, and two side members 316 that depend therefrom. The bottom of side members 316 are advantageously configured for interlocking engagement with an underlying structure (not shown). This arrangement provides a reliable alignment mechanism. The facing or opposed surfaces of side members 316 have spaced teeth 318 that define slots 320.

Figure 4:
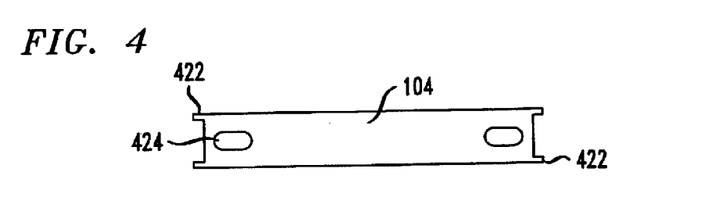
FIG. 4 depicts a horizontally-disposed positioning member that engages the u-shaped support member of FIG. 3.

Support member 102 receives positioning member 104 in slots 320. In particular, slots 320 receive protrusions 422 that depend from the ends of positioning member 104 (see. FIGS. 1, 3 and 4).

Figure 8:
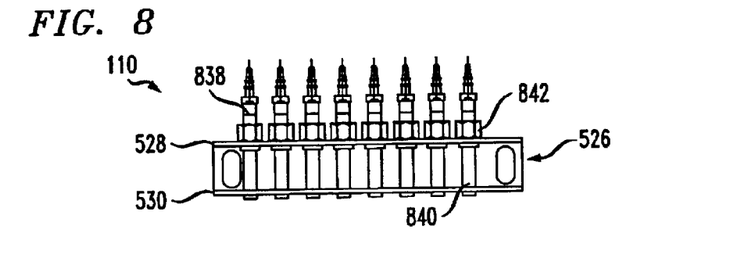
FIG. 8 depicts a multi-channel liquid dispensing head including the valve-support member of FIG. 5, and a plurality of valves and integrated nozzles.

Multi-channel dispensing head 110 is attached to positioning member 104. Specifically, valve-support plate 526 (see FIG. 5), which is an element of multi-channel dispensing head 110 (see FIGS. 1 and 8), is attached to positioning member 104. Other elements of multi-channel dispensing head 110, which are described in detail later in this Specification, include valves 838 and integrated nozzles 840 (see, FIG. 8).

Figure 5:
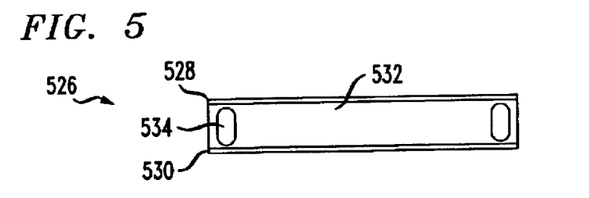
FIG. 5 depicts a valve-support member that receives the dispensing valves.
Figure 6:
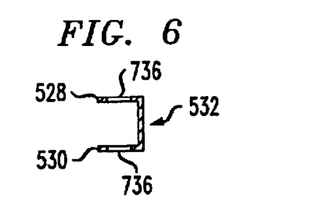
FIG. 6 depicts a cross-sectional side view of the valve-support member of FIG. 5.
Figure 7:
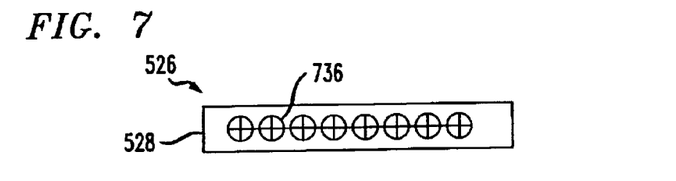
FIG. 7 depicts a plan view of the valve-support member of FIG. 5.

With reference to FIGS. 5 and 6, valve-support plate 526 includes upper receiving portion 528 and lower receiving portion 530 that are connected by side portion 532. Upper receiving portion 528 and lower receiving portion 530 have holes 736 for receiving valves. 838 and nozzles 840 (see FIGS. 7, 8 and 1).

Positioning member 104 includes slots 424, which, in the illustrative embodiment, have an elongate shape. When positioning member 104 engages support member 102, the long axis of each slot 424 is advantageously horizontally disposed (see FIGS. 1 and 3).

Similar to support member 102, valve-support plate 526 includes two slots 534 (see FIGS. 1, 5 and 8) having an elongate shape. In use, slots 424 in positioning member 104 are aligned with slots 534 in valve-support plate 526 (see FIG. 1). Valve-support plate 526 is attached to positioning member 104 by passing a bolt or other engagement member (not shown) through slots 424 and 534. When engaged to positioning member 104, the long axis of each of slots 534 is advantageously vertically disposed (see FIG. 1, etc.).

Slots 424 and 534 function, collectively, as a two axis positioner. In particular, valve-support plate 526 is movable in a transverse direction (ie., right to left or vice-versa in FIG. 1) along the long axis of slots 424 of positioning member 104. Moreover, valve-support plate 526 is also movable in a vertical direction (i.e., up and down in FIG. 1).

Vertical movement is provided by moving valve-support plate 526 along the long axis of slots 534 and/or by altering the vertical placement of positioning member 104 in slots 320. Specifically, protrusions 422 of positioning member 104 can engage slots 320 relatively nearer to the top of side members 316 (ie., near top 314) or relatively nearer to the bottom of side members 316.

In this manner, valve-support plate 526 is suitably positioned in both the transverse and vertical directions to bring nozzles 840 into alignment with a receiver, such as wells 92 of micro-titer plate 90.

In some embodiments of the present invention, longitudinal positioner 212 (see FIG. 2) moves valve-support plate 526 (and positioning member 104) longitudinally. In FIG. 1, longitudinal movement is "out-of-the-page" or vice-versa and, in FIG. 2, longitudinal movement is "right-to-left" and vice-versa. Longitudinal positioner 212 engages valve-support plate 526 (or positioning member 104) near one edge thereof (ie., in FIG. 1, either towards the left edge or the right edge of plate 526). Consequently, as positioner 212 moves engaged valve-support plate 526, multi-channel liquid dispensing head 110 is "tilted" in the longitudinal direction. This adjustment allows nozzles 840 to be brought into alignment with wells 92 in micro-titer plate 90 if the micro-titer plate is tilted.

Figure 9A:
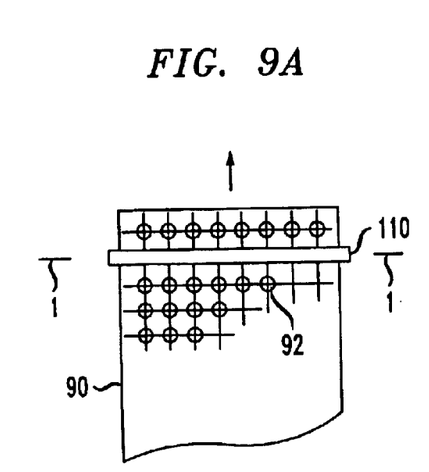
FIGS. 9A–9C depict a receiver that is tilted with respect to the head of FIG. 8.
Figure 9B:
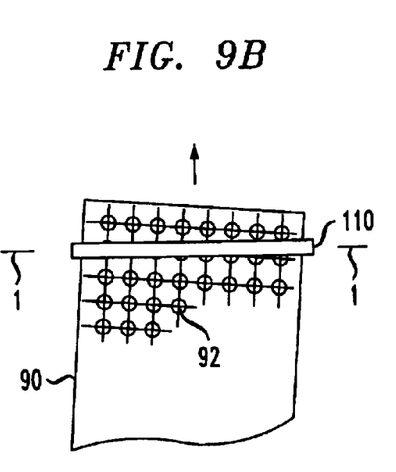
Figure 9C:
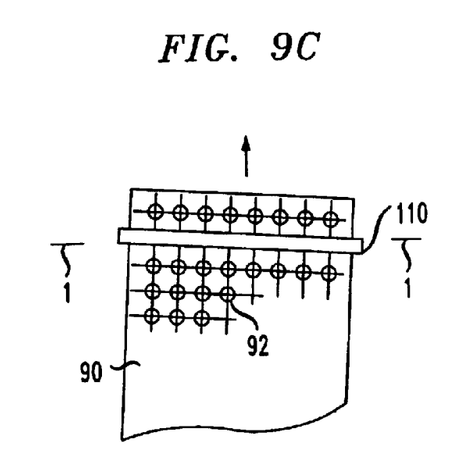

The "tilt" that is imparted to multi-channel liquid dispensing head 110 by longitudinal positioner 212 is depicted, via simplified top view representations, in FIG. 9A–9C. FIGS. 9A–9C depict micro-titer plate 90 moving beneath multi-channel liquid dispensing head 110 so that the sequential rows of wells can receive liquid from nozzles 840 (not shown in FIGS. 9A–9C).

In FIG. 9A, micro-titer plate 90 is oriented (properly) such that sequential rows of wells 92 are aligned in parallel with respect to axis 1—1. Consequentially, as the rows of wells are moved beneath multi-channel liquid dispensing head 110, nozzles 840 align with each of the underlying wells 92.

FIG. 9B depicts a situation wherein micro-titer plate 90 is tilted relative to multichannel liquid dispensing head 110. That is, rows of wells 92 are not parallel with respect to axis 1—1. In this situation, when a row of wells moves into position beneath multi-channel liquid dispensing head 110, nozzles 840 will not align with all of the wells 92 within that row.

FIG. 9C depicts a situation wherein micro-titer plate 90 is tilted, but, in accordance with the present teachings, liquid dispensing head 110 is tilted in complementary fashion, by the action of longitudinal positioner 212, such that nozzles 840 align with all underlying wells 92.

The Dispensing Portion

The dispensing portion of multi-channel liquid dispenser 100 includes reservoir 106, fluid-delivery conduits 108, valves 838, nozzles 840 and other ancillary elements.

In use, reservoir 106 is under pressure. This pressure provides the energy required for dispensing liquid. In one embodiment of the present invention, reservoir 106 is pressurized via gas conduit 848 (see FIGS. 2 and 10). A first end of gas conduit 848 terminates at reservoir 106, and a second end of gas conduit 848 is placed in fluid communication with pressurized gas source (not shown) through operation of a mode selector (not shown), such as a three-way valve and switch. As used herein, the phrase "fluid communication," indicates that fluid (i.e., liquid and/or gas) can flow between two regions.

In some embodiments of the present invention, a suction flow is generated through multi-channel liquid dispenser 100 so that a partial vacuum is drawn through reservoir 106 and fluid-delivery conduits 108. This suction flow allows the dispenser to aspirate (i.e., suck) fluid during a cleaning operation, etc.

To generate a suction flow, a second end of gas conduit 848 is placed in fluid communication with a suction flow generator (not shown) through operation of the aforementioned mode selector (not shown). The suction flow generator can be, for example, a pump, jet ejector or the like.

Figures 10, 11:
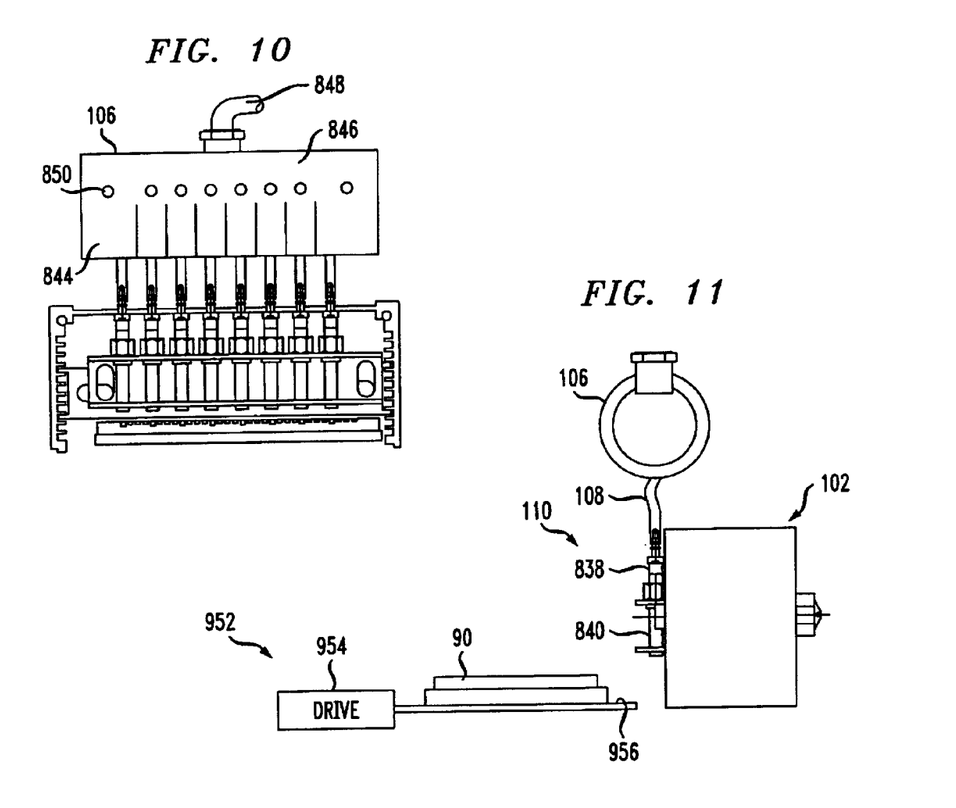
FIG. 10 depicts an illustrative embodiment of multi-channel dispenser/aspirator in accordance with the present invention having a compartmentalized reservoir.
FIG. 11 depicts a further embodiment wherein the multichannel dispenser includes an incremental positioner for advancing a receiver towards the dispensing valves.

With reference to FIG. 10, reservoir 106 advantageously contains multiple internal chambers or compartments 844. One advantage of using multiple chambers 844, in accordance with the present teachings, is that different reagents can be stored in each chamber and subsequently fed to valves 838 for dispensing. Ports 850 are used to fill individual chambers 844.

A second benefit of using multiple internal chambers 844 is that the impact of a failure in any one channel is reduced. In particular, if one valve 838 or liquid channel leaks or otherwise fails, the loss of reagent is limited to the reagent in the associated chamber 844. And this applies to any mode of valve failure or other malfunctions. By contrast, in the case wherein multiple valves are fed by a common reservoir, if one valve were to fail in the open position, all of the reagent in the reservoir would be lost.

In the illustrative embodiment, reservoir 106 has eight chambers to supply eight dispensing channels. Of course, in other embodiments, reservoir 106 is suitably provided with more or fewer internal chambers as is appropriate for the number of dispensing channels in dispenser 100.

Region 846 above chambers 844 is not compartmentalized. Non-compartmentalized region 846 facilitates an even distribution of pressure within reservoir 106, thereby promoting the balanced dispensing of liquids through multiple valves 838. Furthermore, non-compartmentalized region 846 allows for ease in filling reservoir 106 in embodiments in, which a single reagent is used in all chambers 844.

Fluid-delivery conduits 108 place valves 838 in fluid communication with reservoir 106. Fluid-delivery conduits 108 are advantageously very short to reduce the impact of temperature/viscosity fluctuations, internal gas bubbles, elasticity variations of the tubing, and the like. Moreover, short conduits also keep reagent losses to a practical minimum during priming, cleaning, purging and servicing operations. Fluid-delivery conduits having a length in the range of about 5–10 millimeters have been found to be acceptable for such purposes. It will be understood that fluid delivery conduits longer than 5–10 millimeters can be used, but the potential impact of the above-described variations will increase concomitantly. Fluid-delivery conduits 108 are suitably formed from tubing, such as TYGON™ tubing, which is commercially available from Norton Performance Plastics, Akron, Ohio.

Valves 838 control the dispensing operation. The amount of liquid dispensed is advantageously controlled to a specific volume, which is primarily a function of (1) the amount of time that valves 838 are open and (2) the pressure level in fluid-delivery conduits 108 or reservoir 106. To a lesser extent, the dispensed amount of liquid also depends on liquid properties (e.g., viscosity, etc.).

Valves 838 are advantageously "micro" valves, such as are used for print heads in ink-jet printers. Micro-valves are capable of dispensing micro-volumes of fluid in the range of about 20 nano-liters to several micro-liters. Micro-valves are commercially available from The Lee Company of Essex, Conn., and others.

Nozzles 840 are in fluid communication with valves 838 and ultimately dispense the liquid stored in reservoir 106 into a receiver, such as wells 92 of micro-titer plate 90. In some embodiments of the present invention, nozzle 840 is an integral portion of valve 838 (i.e., it is obtained from a supplier as a combined valve/nozzle), while in other embodiments, separate valves and nozzles are suitably used.

In some embodiments of the present invention, micro-titer plate 90 is advanced toward multi-channel liquid dispensing head 110 via incremental positioner 952, which is represented by drive 954 and stage 956 (see FIG. 11). Micro-titer plate 90 rests on stage 956 and drive 954 advances stage 956 towards multi-channel liquid dispensing head 110.

One incremental positioner suitable for use in this service is the positioner disclosed applicant's co-pending patent application entitled "Article Comprising an Incremental Positioner," which was filed on Sep. 14, 1999 as Ser. No. 09/395,132 and is incorporated herein by reference. That positioner is reliable, fast and inexpensive, and is therefore advantageously used. Other more complicated arrangements for incremental positioning, such as a stepper motor used in conjunction with a processor, as is known in the art, may suitably be used, as well.

Flow Control Features

One or more of the following optional flow-control features are advantageously incorporated into liquid dispenser 100 to improve the accuracy of the fluid dispensing operation.

If liquid is dispensed squarely into (ie., orthogonal to the bottom of) well 92 of micro-titer 90, it can splash off of the bottom of the well. In fact, a portion of the dispensed liquid is likely to splash out of the well. The result of this is, of course, that the desired amount of liquid is not retained by the well and, furthermore, other wells might be contaminated with the splashed liquid.

Moreover, when liquid is squarely dispensed into well 92, an air bubble(s) is often trapped. The bubble may burst after some time, thereby causing liquid to splash out of well 92. Alternatively, the bubble might not burst, and the presence of the bubble can interfere with analyses.

This problem is addressed, in accordance with the present invention, by varying the angle at which liquid is dispensed into a well, as described below.

In some embodiments of the present invention, fasteners, such as nuts 842, attach valves 838 and integrated nozzles 840 to valve-support plate 526. Nozzles 840 are received by holes 736 in upper receiving portion 528 and lower receiving portion 530 of valve-support plate 526 (see, e.g., FIG. 8). The diameter of holes 736 that receive nozzles 840 is substantially larger than the outside diameter of the nozzles.

Figure 12:
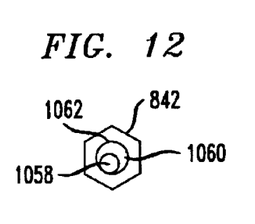
FIG. 12 depicts a nut with an eccentrically-disposed hole.

Referring now to FIG. 12, each fastener (e.g., nut 842) receives a valve 838 and integrated nozzle 840 in eccentrically disposed hole 1058. In one embodiment, eccentrically disposed hole 1058 is provided by placing bushing 1060 (having an eccentrically disposed hole) within the centrally located hole 1062 of a standard nut As nut 842 is rotated, engaged valve 838 and nozzle 840 "tilt" relative to the vertical. Such tilting is facilitated by oversized holes 736. This tilting is depicted, figuratively, in FIG. 13 wherein nozzle 840 is not aligned with vertical axis 2—2.

Figure 13:
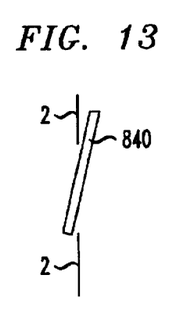
FIG. 13 depicts a nozzle tilted relative to the vertical by adjusting the nut of FIG. 12.

The ability to tilt valves 838 and integrated nozzles 840 in this manner allows liquid to be dispensed along an off-normal path towards the bottom of wells 92. Consequently, a dispensed liquid droplet(s) ricochets off the bottom of well 92 and towards a side-wall thereof. The droplet ricochets off the side wall, now moving in the direction opposite to which it entered the well. When delivered in this manner, there is a substantially reduced tendency to trap air. Moreover, the reflections dissipate the energy of the droplet such that liquid tends to remain in the well.

The following optional features are disposed in/on fluid-delivery conduits 108. In embodiments in which such optional features are included in dispenser 100, fluid-delivery conduits 108 are suitably lengthened to accommodate such elements. The previously described drawbacks that result from increasing the length of fluid-delivery conduits 108 are tempered by these optional flow control features.

Illustrative dispenser 100 has eight channels for dispensing liquid. It will be appreciated that differences might arise in the operating behavior of the various channels, especially over the course of a usage cycle. Such differences might be due, for example, to variations in valve performance from channel to channel, or to channel-to-channel variation in the degree to which fluid delivery conduits, valves and/or nozzles are occluded.

To this end, adjustable orifices or pinch valves 1164 are advantageously provided in fluid delivery conduits 108 near where they join valves 838 (see FIG. 12). Adjustable orifices 1164 are operable to affect dispensing speed and therefore able to synchronize the dispensing operation of all channels of dispenser 100 to compensate for any channel-to-channel variations that might occur.

The following flow-control features are described in further detail in applicant's co-pending U.S. patent application entitled "Article and Method for Flow Control in Fluid Dispensing Devices," which was filed on Sep. 14, 1999 as Ser. No. 09/395,383. This application is incorporated herein by reference.

Dispensers that provide, a constant "re-supply" of fluid to replace dispensed fluid, such as illustrative dispenser 100 depicted in FIG. 1, are susceptible to a characteristic error. The error is related to certain performance attributes of the valve. In particular, the amount of fluid that is dispensed from such dispensers is proportional to the amount of time that the valve is open. The valves (e.g., valves 838) that are typically used in such dispensers exhibit a rapid response to an impulse (e.g., voltage) to open, but the closure response tends to be less precise, as a function of the spring used in the valve.

Figure 14:
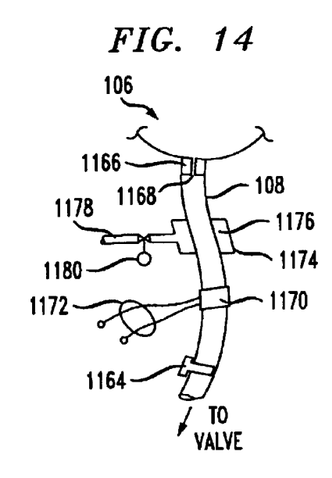
FIG. 14 depicts various optional flow control/flow regulation features for use with fluid-delivery conduits.

With reference to FIG. 14, in some embodiments of the present invention, a flow restriction, such as restriction orifice 1166, is disposed in fluid conduit 108. The flow restriction is advantageously disposed at the input (ie., at the interface between reservoir 106 arid the fluid conduit 108) of fluid conduit 108. In some embodiments, fluid conduit 108 is elastic, or has a region that is elastic, such that it functions as an accumulator or bladder. Restriction orifice 1166 has an outlet orifice 1168 that is smaller than the opening of dispensing valves 838. As a result, fluid is re-supplied to fluid conduit 108 more slowly than it is dispensed through valve 838. Errors resulting from any delay in valve closure are therefore reduced in magnitude since the flow rate to valve 838 is reduced by limiting the resupply rate.

It is advantageous to monitor the pressure in fluid conduit 108 as it falls and rises during respective dispensing and refilling cycles. Such pressure data can be correlated to an amount of fluid dispensed and also provide indications of operational problems (e.g., occlusions in the fluid conduit 108).

Consequently, in some embodiments of the present invention, pressure sensing is provided. Dynamic pressure sensors (e.g., piezo resistive sensors, etc.) are advantageously used for such pressure sensing since they are much less expensive (ie., about an order of magnitude) than static pressure sensors and typically provide sufficient information. At least a portion of fluid conduit 108 must be elastic to use a dynamic pressure sensor.

In an embodiment depicted in FIG. 14, dynamic pressure sensor 1170 is operatively engaged to an elastic region of fluid conduit 108. Leads 1172 from sensor 1170 connect to appropriate electronics (not shown) for processing sensor data and displaying and/or recording such data. In some embodiments, the present dispenser includes both a restriction orifice 1166 and dynamic pressure sensor 1170 to improve accuracy.

Over time, the performance characteristics of a fluid dispenser may change. For example, elastic conduit may lose resilience over time. Moreover, variations in fluid parameters (e.g., changes in viscosity, etc.) from use-to-use may affect the fluid dynamics within the dispenser and hence the dispensing operation itself. To the extent that such a change in elasticity or in fluid parameters varies from a baseline condition, there will be a difference between the actual amount and the desired amount of liquid dispensed.

In one embodiment, pinch valve 1164 described above is operable to compensate for such changes. In a second embodiment in accordance with the present teachings, a resilience-adjusting element is operable to adjust the "resilience" or "elasticity" of an elastic region of fluid conduit 108. By appropriately adjusting the resilience-adjusting element, dispenser operation can be maintained at a baseline notwithstanding changed system conditions. Such adjustment is best performed via trial and error, wherein the resilience-adjusting element is changed and the dispensed volume measured. The resilience-adjusting element is adjusted until the proper volume is dispensed. Of course, a user can adjust valve operation and/or pressure to affect changes in the dispensed volume, as well.

In the embodiment depicted in FIG. 14, the resilience-adjusting element comprises an enclosure 1174 that defines a pressure-tight chamber surrounding at least a portion 1176 of an elastic region of fluid conduit 108, and a pressure-adjustment element. Increasing the pressure within chamber effectively increases the resilience of the enclosed region of fluid conduit 104.

In some embodiments, the pressure-adjustment element is realized by gas supply conduit 1178 that delivers gas (e.g., nitrogen, etc.) to enclosure 1174, and pressure regulator 1180. Additionally, an optional vacuum-flow conduit (not shown) for drawing a partial vacuum can be connected to enclosure 1174.

In a further embodiment, dispenser 100 incorporates a flow monitor/controller for monitoring and controlling liquid flow, as described in detail in applicant's co-pending U.S. patent application entitled "Article and Method for Predictable Dispensing of Small Liquid Volumes," which was filed on Jan. 31, 2000 as Ser. No. 09/494,387. This application is incorporated herein by reference.

As used in this Specification, the phrase "flow control features" refers to any of the features described in this section (i.e., eccentrically-disposed hole in fastener, pinch valves, restriction orifice, dynamic pressure sensing, resistance-adjusting element and flow monitor/controller) that are operable to control liquid flow.

I claim:

1. An article comprising:
    a positioning plate, wherein said positioning plate has a first end, a second end, and a first elongated opening, and wherein said first elongated opening has a long axis that is aligned with a first direction;
    a support plate, wherein:
        said support plate has a first end, a second end, and a second elongated opening;
        said second elongated opening in said support plate has a long axis that is aligned with a second direction;
        said first direction and said second direction are not coincident; and
        said positioning plate and said support plate are engaged to one another via said first elongated opening and said second elongated opening; and
    a positioner, wherein said positioner mechanically couples to one of said first end or said second end of at least one of either said positioning plate or said support plate, and wherein said positioner moves said mechanically coupled first end or second end in a third direction that is different from said first direction and said second direction.

2. The article of claim 1 wherein said first direction and said second direction are orthogonal to one another and define a first plane.

3. The article of claim 2 wherein said third direction does not lie in said first plane.

4. The article of claim 2 wherein said third direction is orthogonal to said first plane.

5. The article of claim 2 further comprising a support member, wherein said support member is disposed on an underlying surface, and wherein said support member and said positioning plate engage one another, such that said support member supports said positioning plate and said support plate above said underlying surface.

6. The article of claim 5 wherein said support member comprises two, spaced, upright members, wherein said two upright members are suitably dimensioned and spaced for receiving said first and second end of said positioning plate.

7. The article of claim 6 wherein facing sides of said upright members have a plurality of slots for engaging said first end or said second end of said positioning plate, and wherein selection of particular slots from said plurality of slots controls a height of said positioning plate above said underlying surface.

8. The article of claim 7 wherein said long axis of said second elongated opening in said support plate is aligned with a vertical direction, thereby providing an ability to adjust a height of said support plate above said underlying surface independently of said height of said positioning plate.

9. The article of claim 1 wherein said support plate comprises:
    a major surface in which said second elongated hole is disposed;
    an upper marginal portion that depends from a top of said major surface, wherein said upper marginal portion comprises an array of holes;
    a lower marginal portion that depends from a bottom of said major surface, wherein said lower marginal potion comprises an array of holes, and wherein said array of holes in said lower marginal portion align with said array of holes in said upper marginal portion.

10. The article of claim 9 further comprising:
    a plurality of valves; and
    a plurality of nozzles, wherein each of said valves is coupled to one of said nozzles;
        wherein said nozzles are received in said array of holes in said upper marginal portion and said lower marginal portion of said support plate.

11. The article of claim 10 further comprising a plurality of fasteners for fastening said valves and said nozzles to said support plate, wherein said fasteners have eccentrically disposed holes that receive said valves or said nozzles, such that when said fasteners are rotated, said valves and said nozzles tilt relative to said second direction.

12. The article of claim 10 further comprising a plurality of fluid-delivery conduits, wherein said fluid-delivery conduits are in fluid communication with said plurality of valves.

13. The article of claim 12 further comprising a reservoir having a plurality of chambers that are in fluid communication with said plurality of said fluid-delivery conduits.

14. An article comprising a positioner having multiple degrees of freedom, comprising:
    a first plate, wherein said first plate has a first elongated opening having a long axis that is aligned with a first horizontal axis;

a second plate, wherein:
  said second plate has a second elongated opening having a long axis that is aligned with a vertical axis;
  said first plate and said second plate are coupled to one another via said first elongated opening and said second elongated opening;
a positioner, wherein:
  said positioner moves an end of said first plate and said second plate along a second horizontal axis;
  said second horizontal axis is out-of-plane relative to a major surface of said first plate; and
  due to movement of said end of said first plate and said second plate, said major surface of said first plate moves to an orientation that Is not parallel to its orientation before said movement.

15. The article of claim 14 further comprising a support member, wherein said support member receives said first plate at a variable height.

16. The article of claim 14 wherein said second plate comprises:
  a major surface in which said second elongated hole is disposed;
  an upper marginal portion that depends from a top of said major surface, wherein said upper marginal portion comprises an array of holes; and
  a lower marginal portion that depends from a bottom of said major surface, wherein said lower marginal potion comprises an array of holes, and wherein said array of holes in said lower marginal portion align with said array of holes in said upper marginal portion to define a plurality of vertically-disposed receivers.

17. The article of claim 16 further comprising:
a plurality of valves; and
a plurality of nozzles, wherein each of said valves is coupled to one of said nozzles, wherein:
  said nozzles are received by said plurality of vertically-disposed receivers; and
  a diameter of said holes that define said vertically-disposed receivers is larger than an outside diameter of said nozzles.

18. The article of claim 17 further comprising a plurality of fasteners for fastening said valves and said nozzles to said vertically-disposed receivers of said second plate, wherein said fasteners have eccentrically-disposed holes that receive said valves or said nozzles, such that when said fasteners are rotated, said valves and said nozzles tilt relative to said vertical direction.

* * * * *